(12) United States Patent
Neyens et al.

(10) Patent No.: US 10,024,732 B2
(45) Date of Patent: Jul. 17, 2018

(54) FEEDING DEVICE FOR AN OPTICAL FIBER FOR MEASURING THE TEMPERATURE OF A MELT

(71) Applicant: Heraeus Electro-Nite International N.V., Houthalen (BE)

(72) Inventors: Guido Jacobus Neyens, Opoeteren (BE); Michel Thys, Koersel (BE); Frank Stevens, Hasselt (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 256 days.

(21) Appl. No.: 15/007,986

(22) Filed: Jan. 27, 2016

(65) Prior Publication Data

US 2016/0216162 A1    Jul. 28, 2016

(30) Foreign Application Priority Data

Jan. 28, 2015    (EP) .................................... 15152833

(51) Int. Cl.
*G01K 11/32* (2006.01)
*G01N 33/20* (2006.01)
(Continued)

(52) U.S. Cl.
CPC ............. *G01K 11/32* (2013.01); *B65H 57/12* (2013.01); *B65H 75/4402* (2013.01);
(Continued)

(58) Field of Classification Search
CPC ........ G01K 11/32; B65H 57/12; B65H 57/14; B65H 57/18; B65H 57/26; B65H 59/00;
(Continued)

(56) References Cited

U.S. PATENT DOCUMENTS 2,417,818 A    3/1947    Stomski et al.
2,716,008 A    8/1955    Taylor
(Continued)

FOREIGN PATENT DOCUMENTS

CN    104132750 A    11/2014
DE    2721616 A1    11/1918
(Continued)

OTHER PUBLICATIONS

Examination Report dated Oct. 31, 2016 in KR Application No. 10-2016-0010517.

(Continued)

*Primary Examiner* — Lisa Caputo
*Assistant Examiner* — Philip Cotey
(74) *Attorney, Agent, or Firm* — Panitch Schwarze Belisario & Nadel LLP

(57) ABSTRACT

A feeding device for feeding an optical fiber from a coil and for recoiling unused fiber for use in an apparatus for measuring the temperature of a melt is provided. The feeding device includes a support for a coil, a feeding mechanism for decoiling the optical fiber from the coil and recoiling the optical fiber, at least one motor for driving the feeding mechanism, and a load for the optical fiber which avoids a spring back effect of the optical fiber from the coil. Blockage is avoided when decoiling and recoiling the optical fiber from the coil.

12 Claims, 6 Drawing Sheets

(51) Int. Cl.
*G01J 5/00* (2006.01)
*G01J 5/08* (2006.01)
*G01J 5/04* (2006.01)
*G01J 5/02* (2006.01)
*B65H 57/12* (2006.01)
*B65H 75/44* (2006.01)
*G02B 6/44* (2006.01)

(52) U.S. Cl.
CPC .............. *G01J 5/004* (2013.01); *G01J 5/0205* (2013.01); *G01J 5/04* (2013.01); *G01J 5/041* (2013.01); *G01J 5/048* (2013.01); *G01J 5/0821* (2013.01); *G01N 33/206* (2013.01); *B65H 2701/32* (2013.01); *G02B 6/4457* (2013.01); *G02B 6/4459* (2013.01)

(58) Field of Classification Search
CPC . B65H 75/4402; B65H 2701/32; G01J 5/004; G01J 5/0205; G01J 5/04; G01J 5/041; G01J 5/048; G01J 5/0821; G01N 33/206; G02B 6/4457; G02B 6/4459
See application file for complete search history.

(56) References Cited

U.S. PATENT DOCUMENTS

| | | | |
|---|---|---|---|
| 4,402,790 A | 9/1983 | Lynn et al. | |
| 4,737,038 A * | 4/1988 | Dostoomian | G01J 5/0037 250/577 |
| 4,742,973 A | 5/1988 | Stomski et al. | |
| 5,585,914 A * | 12/1996 | Yamasaki | G01J 5/02 356/44 |
| 5,944,865 A * | 8/1999 | Do | C03C 25/108 65/381 |
| 6,227,702 B1 * | 5/2001 | Yamada | G01J 5/041 266/88 |
| 6,578,599 B1 | 6/2003 | Ura | |
| 6,795,633 B2 | 9/2004 | Joseph, II | |
| 9,726,545 B2 * | 8/2017 | Neyens | G01J 5/004 |
| 2005/0279183 A1 * | 12/2005 | Neyens | C21C 5/4673 73/866 |
| 2014/0321504 A1 | 10/2014 | Neyens et al. | |
| 2016/0216161 A1 * | 7/2016 | Neyens | G01K 11/32 |

FOREIGN PATENT DOCUMENTS

| | | |
|---|---|---|
| DE | 1024913 B | 2/1958 |
| EP | 2799824 A1 | 11/2014 |
| GB | 1071784 A | 6/1967 |
| JP | H0712650 A | 1/1995 |
| JP | H09101206 A | 4/1997 |
| JP | H09280958 A | 10/1997 |
| KR | 20140130075 A | 11/2014 |

OTHER PUBLICATIONS

Extended Search Report dated Jul. 20, 2015 in EP Application No. 15152833.8.
Office Action dated Jan. 25, 2017 in CA Application No. 2915481.
Extended Search Report dated Mar. 14, 2017 in EP Application No. 15152833.8.
Office Action dated Mar. 20, 2018 in CN Application No. 201610059541.0.

* cited by examiner

FEEDING DEVICE FOR AN OPTICAL FIBER FOR MEASURING THE TEMPERATURE OF A MELT

BACKGROUND OF THE INVENTION

The present invention relates to a feeding device for feeding an optical fiber from a coil and for recoiling unused fiber for use in an apparatus for measuring the temperature of a melt. The device according to the present invention comprises a support for a coil, a feeding mechanism for decoiling the optical fiber from the coil and recoiling the optical fiber, and at least one motor for driving the feeding mechanism. The present invention also relates to an apparatus for measuring the temperature of a melt, particularly of a molten metal, for example molten steel, with an optical fiber.

As known from EP 2 799 824 A1, an Electric Arc Furnace (EAF) process for the production of molten steel is a batch process made up of the following operations: furnace charging of metallic components, melting, refining, de-slagging, tapping and furnace turnaround. Each batch of steel, called a heat, is removed from the melting furnace in a process called tapping and hence, a reference to the cyclic batch rate of steel production is commonly a unit of time termed the tap-to-tap time. A modern EAF operation aims for a tap-to-tap cycle of less than 60 minutes and is more on the order of 35-40 minutes.

EP 2 799 824 A1 relates to a robotic immersion device for measuring the temperature in a metallurgical vessel using a molten metal immersed consumable optical fiber and immersion equipment capable of inserting a temperature device through the side wall of an EAF to a predictable molten steel immersion depth with a temperature-to-temperature measuring frequency of less than 20 seconds. The ability to sample on-demand, singularly or in rapid succession, allows a measuring strategy that can update a mathematical predictive model for EAF operations at key times during the process with the ability to measure in rapid succession providing near continuous temperature data at a low cost.

EP 2 799 824 A1 discloses providing a spot measurement rather than a continuous measurement. EP 2 799 824 A1 discloses a low cost solution for temperature measurements suitable to be utilized at a sufficiently high sampling frequency to meet the updating demands of the mathematical models of the EAF melting process, while solving the problems associated with immersed optical fiber in harsh environments. The solution provides a near continuous temperature measuring output comprised of immersing an optical fiber into the molten metal through the slag covering without first contacting the slag, maintaining a predetermined immersion depth during the measuring period by controlled feeding, protecting the non-immersed portion against devitfication in the high ambient heat of the EAF interior, removing and recoiling unused fiber after the measurement, measuring the bath level upon recoiling and an immersion equipment for repeating the measuring processes always duplicating the initial starting conditions.

Feeding the optical fiber, particularly a metal coated optical fiber, from the coil and recoiling unused fiber after the measurement may have the effect that the optical fiber becomes entangled for example due to an elastic spring back effect. For this reason, the feeding machine known from EP 2 799 824 A1 is adapted with additional means to avoid an elastic spring back effect from the coil or spool. The feeding machine comprises two servo motors or feeding motors to control the fiber movement. One feeding motor takes care of the de-coiling and recoiling of the fiber and pre-feeds fiber in such a way that the feeding motor can accelerate very fast.

An apparatus for automatically uncoiling a spool of wire is known from U.S. Pat. No. 4,742,973. An arrangement for facilitating the withdrawal of flexible material is known from U.S. Pat. No. 2,716,008. Temperature measurement systems for high temperature object employing an optical fiber are known from JP 9101206 A, JP 701 26 50 A and JP 9280958 A.

It is an objective of the present invention to avoid blockage when decoiling and recoiling a fiber from a coil of a feeding device for feeding an optical fiber.

BRIEF SUMMARY OF THE INVENTION

An embodiment of the present invention relates to device for feeding an optical fiber from a coil and for recoiling unused fiber. The device comprises a support for a coil, a feeding mechanism for decoiling an optical fiber from the coil and recoiling the optical fiber, and at least one motor for driving the feeding mechanism. The device comprises a load for the optical fiber which avoids a spring back effect of the optical fiber from the coil. As a result, a blockage is avoided when decoiling and recoiling the fiber.

A weight attached to the optical fiber may act as the load. In addition, or as an alternative, a spring may act as the load.

As a rule, the optical fiber is metal coated and the diameter of the metal coated fiber is, as a rule, more than 1 mm, for example 1-15 mm, preferably 1-3 mm.

Preferably, the weight acting as the load is a guide for the optical fiber in the form of a flexible tube, in order to provide a simple technical solution which works in a reliable manner.

In a preferred embodiment, the flexible tube is formed from metal. As a rule, the weight of the flexible tube is sufficient for providing a load which avoids the spring back effect.

In a preferred embodiment, a degree of stiffness of the flexible tube supplies resistance to its bending. That is, the flexible tube has a spring type behavior which provides a load to avoid the spring back effect.

In a preferred embodiment, the flexible tube comprises a non-fixed end for providing an appropriate load which avoids the spring back effect, and thus avoids a blockage.

Preferably, the non-fixed end of the flexible tube ends below the axis of the coil when the coil has been inserted into the support, in order to provide an appropriate load in a technical simple manner.

In a preferred embodiment, the inner diameter of the flexible tube is more than 10 mm, preferably more than 30 mm and/or the length of the flexible tube is more than 100 mm, preferably more than 200 mm. On one hand, the weight of the flexible tube is, as a rule, sufficient due to these dimensions in order to provide a load which avoids the spring-back effect. On the other hand, an inner diameter of more than 10 mm, preferably of more than 30 mm (which is, as a rule, much larger than the outer diameter of a metal coated optical fiber) avoids a pinch effect, and thus a blockage in the course of de-coiling and recoiling the fiber.

For this reason, the inner diameter of the flexible tube is, in a preferred embodiment, at least five times larger than the outer diameter of the metal coated optical fiber, preferably at least ten times larger.

In a preferred embodiment, the device comprises a housing which covers the support for the coil and the load for the optical fiber. As a result, the coil and the load for the optical fiber are protected against an outer influence, particularly a disruption which may stop the process of de-coiling and recoiling the fiber. Thus, this embodiment contributes to the solution of the above-stated objective of the present invention.

In a preferred embodiment, the housing is a cabinet especially comprising a first accessible compartment for the coil and a second compartment for an electrical equipment of the device. In this way, the coil, and thus the optical fiber, is separated from other parts in order to solve the above-stated objective of the present invention in a more reliable manner. The first compartment is accessible for an end-user and thus is not closed, for example, by a lock. As a result, an end user can insert or replace a coil if necessary.

Preferably, the second compartment comprising an electrical equipment of the feeding device is closed, for example, by a door lock. As a result, the electrical equipment is well protected, which avoids a disturbance for example due to misuse.

In a preferred embodiment, the cabinet, preferably at least and/or only the first compartment of the cabinet, is air-conditioned. In this way, the first compartment is protected against overheating. Overheating may disturb the process of de-coiling and recoiling the fiber. Thus, this embodiment also contributes to the solution of the above-stated objective of the present invention. Further, the air conditioning prevents condensation. As a result, erroneous measurements are avoided.

The present invention also refers to a robotic immersion device comprising the feeding device. In a preferred embodiment, the robotic immersion device comprises a disposable guiding tube, having an immersion end and a second end, opposite to the immersion end, whereby the optical fiber can be partially arranged in the disposable optical guiding tube. The inner diameter of the disposable guiding tube is bigger than the outer diameter of the optical fiber. At least one elastic plug is arranged at the second end of or within the disposable guiding tube. The optical fiber is fed through the elastic plug reduces a gap between the optical fiber and the disposable guiding tube. There is a need for this robotic immersion device to decoil and recoil the optical fiber in a very fast manner. For this reason, the robotic immersion device preferably comprises a feeding device according to the present invention.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
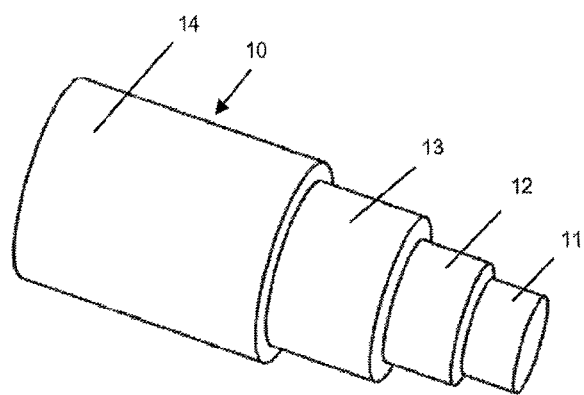
FIG. 1 shows a consumable optical fiber.

FIG. 1 shows a consumable metal coated optical fiber 10, typically employed in the measurement of liquid metals. The metal coated optical fiber 10 comprises an optical fiber 11, a jacket 12 covering the optical fiber 11 and a protective metal tube 14 covering the surface of the plastic jacket 12. The optical fiber 10, typically a graded index multi-mode fiber, is made of quartz glass with an inner core 11 (diameter of 62.5 µm) and an outer cladding 12 (diameter of 125 µm) and is covered with a polyimide or similar material 13. The protective metal tube 14 is typically stainless steel and has a 1.32 mm outer diameter (OD) and a 0.127 mm wall thickness. Although a metal covered optical fiber is preferred, additional embodiments where components 14 and/or 13 are replaced by a singular plastic material do not depart from the intended invention.

Figure 2:
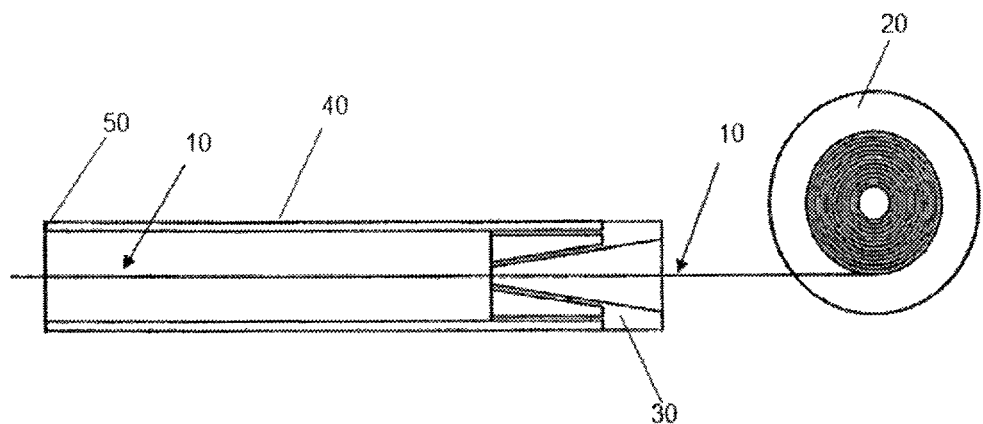
FIG. 2 shows the leading section of a metal coated optical fiber.

FIG. 2 shows the leading section 10 of a metal coated optical fiber 10, as fed from a spool 20 through a gas retaining elastic plug 30, affixed to the opposite immersion end 50 of an outer disposable guiding tube 40. The metal coated optical fiber 10 and the outer disposable guiding tube 40 are not in a fixed arrangement and, as such, can move independent of each other and thus can be independently inserted through the slag layer 51 and into the molten bath 52 at different velocities, while maintaining a gas seal 31 at the opposite end. The disposable guiding tube 40 is preferably low carbon steel having a wall thickness of 0.8 to 1 mm, but may be selected from a variety of metal materials, as well as ceramics and glasses, cardboard and plastics or a combination of materials. In the case that the disposable guiding tube 40 is selected from a material that reacts with the molten bath, it is advisable that the immersion portion 50 is prepared in a way that it does not splash molten metal on the inside of the disposable guiding tube 40 by the application of coating or coverings of a materials known in the art for the purpose of splash reduction.

Immersing the open ended outer disposable guiding tube 40 in the steel through the slag layer 51 without the plug 30 will result in ingress of slag and steel in this tube. Molten slag resulting from the refining process is high in oxides, such as iron oxide which is easily absorbed into the optical fiber structure. The fiber 10 fed through the outer disposable guiding tube 40 containing slag and steel will be damaged before reaching the open end of the outer disposable guiding tube 40.

In a preferred embodiment, the outer disposable guiding tube 40 is 2 m long with an immersion depth of 30 cm and open at both ends, and the upwelling of molten material inside the outer disposable guiding tube 40 will be 30 cm. In case of a closed end outer disposable guiding tube 40, the upwelling will be approximately 16 cm. This is calculated ignoring the gas expansion of the enclosed air which will undergo expansion due to an increase in its temperature. Tests show that the steel ingress can be minimized by reducing the air gap between the inner diameter (ID) of the outer disposable guiding tube 40 and the outer diameter (OD) of the optical fiber 10 metal covering. It is particularly preferred to reduce this gap to the minimum. However, practically, for tubes with an ID of 10 mm, this gap should be less than 2 mm², preferably less than 1 mm². Tubes with a smaller ID would allow for a bigger gap due to the faster heating rate of the enclosed air.

One of the preferred features of the immersion device is to avoid molten ingress utilizing the expansion of the gas contained in the disposable guiding tube 40. The use of an elastic plug 30 to effectively seal the end opposite the immersion end of a certain sealing quality will ensure that gas will bubble out of the immersed end during immersion, thus keeping the disposable guiding tube 40 clear.

Notwithstanding, any means of creating an overpressure in the disposable guiding tube 40 while immersing also avoids steel ingress, such as an internal coating of a material vaporous at minimal temperatures. A prominent concept towards creating a positive pressure in the outer disposable guiding tube 40 is to avoid the upwelling and intrusion of metal, slag or other contaminants inside of the disposable guiding 40 tube that could impede the free feeding of the metal coated fiber 10.

The plug 30 should be suitably elastic in order to compensate for an un-ideal optical fiber end resulting from the prior immersion. In the preferred embodiment, plug 30 is replaced with each outer disposable guiding tube 40. Each replacement assures a proper seal. However, the plug 30 could be constructed in such a way as to be reused with multiple outer disposable guiding tubes and replaced as a matter of maintenance. The preferred location of the plug 30 at the terminal end of the outer disposable guiding tube 40 is selected for ease of application. However, placing the plug 30 closer to the immersion end is equally acceptable and will accomplish a superior overpressure during immersion, aiding the error free immersion of the optical fiber 10. The design of the plug 30 facilitates its placement at the extremity of disposable guiding tube 40, showing a lip that rests upon the tube end. Other configurations are possible. The exact embodiment of the plug 30 should reflect the ease of positioning and location of its position, without departing for the main purpose of the plug to restrict the escape of air in the outer tube, thus ensuring a build-up of inner pressure.

The steel ingress in the steel tube while immersing in the steel tube increases with:
- an increase of the immersion depth;
- an increase of the tube length;
- an increase of the air gap (at the other end);
- a lower bath temperature;
- a thicker wall thickness; and/or
- a higher oxygen content of the steel bath.

Figure 3A:
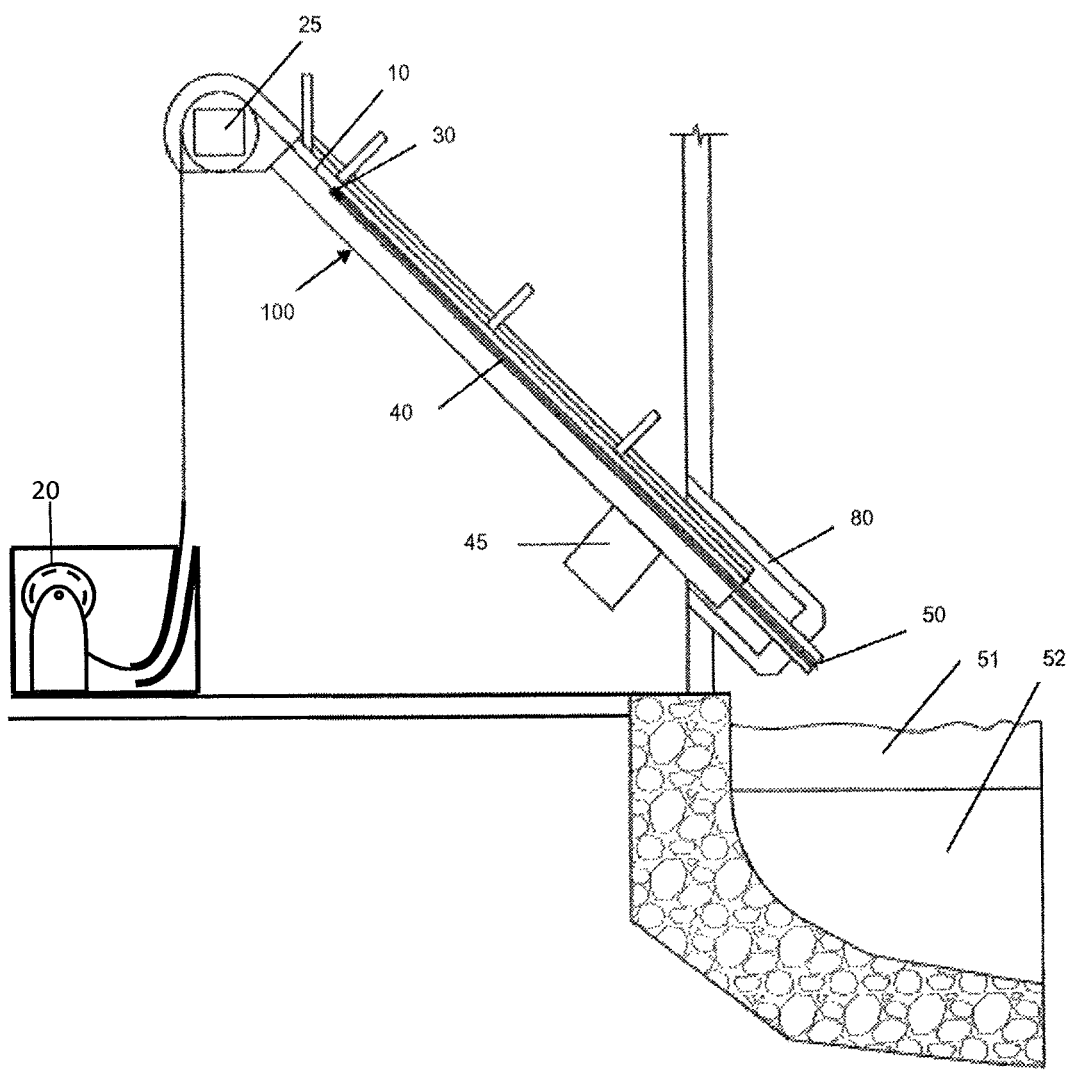
FIG. 3a shows an immersion device before immersing of the optical fiber.
Figure 3B:
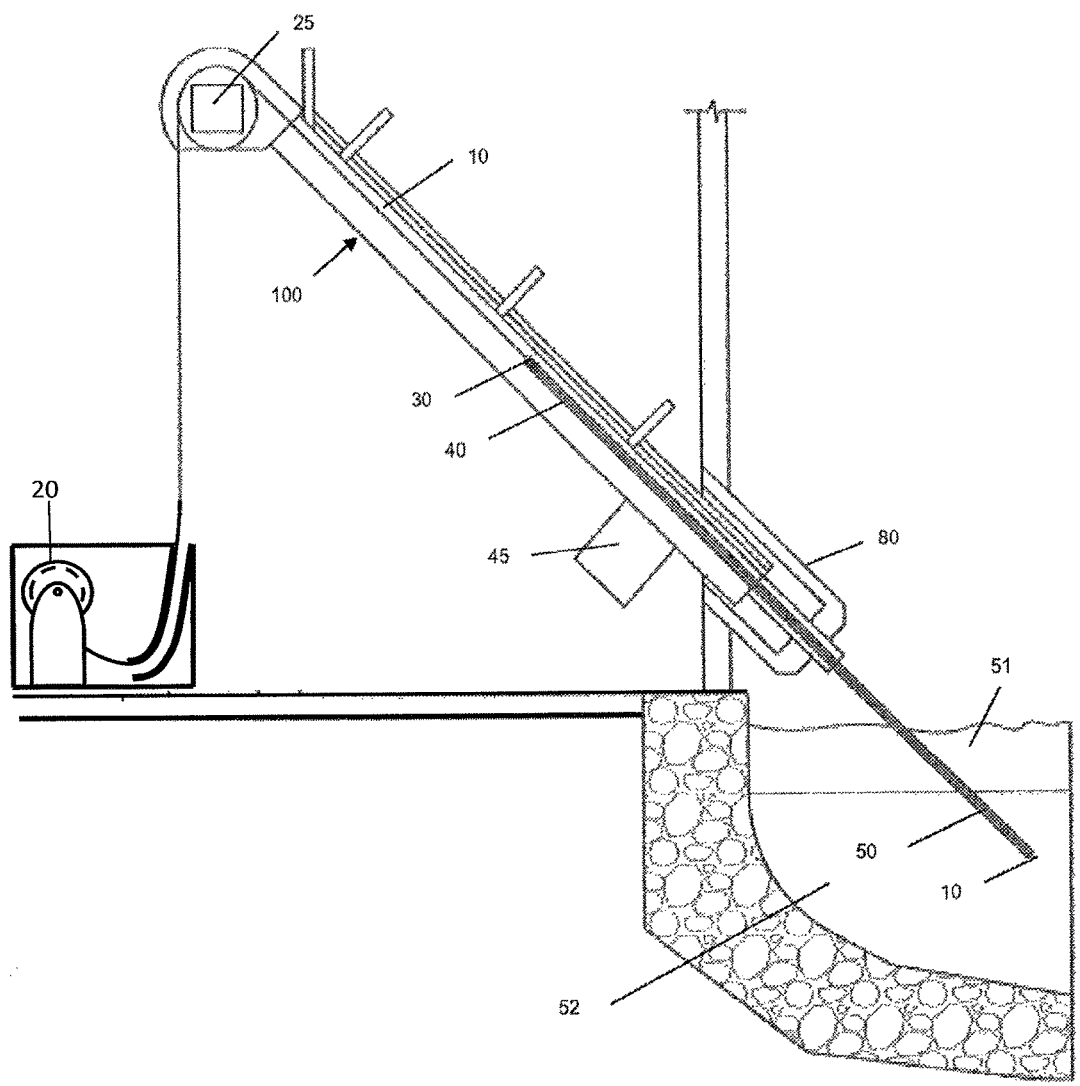
FIG. 3b shows the immersion device of FIG. 3a after immersing of the optical fiber.
Figure 3C:
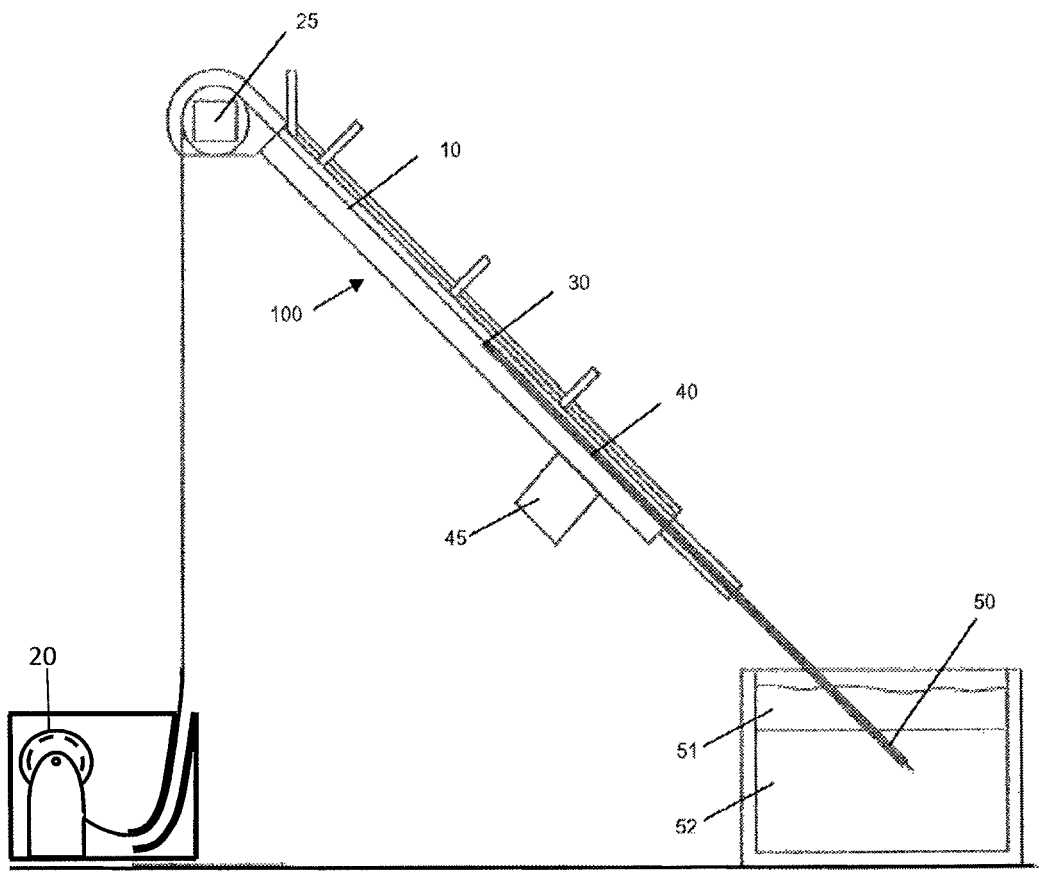
FIG. 3c shows the immersion device according to FIG. 3b with a different melt container, such as a molten metal ladle or tundish.

The immersion device is described in FIG. 3. Machine 100 is suitably constructed and instrumented in such a manner that assembly plug 30 is aligned to outer disposable guiding tube 40 so the metal coated optical fiber 10 can be inserted through plug 30 into the interior of the outer disposable guiding tube 40. Both the outer disposable guiding tube 40 and the metal coated optical fiber 10 are fed at approximately 2000 mm/s through the side wall of an EAF through suitable access panels 80. These panels 80 are not part of the machine 100. The machine 100 has independent 100% reversible drive or feeding motors 25 and 45. Motor 25 drives the optical fiber 10 and motor 45 drives the disposable guiding tube 40, so that the velocity of the outer disposable guiding tube 40 in either direction is independent of the velocity of the optical fiber 10 in either direction.

The machine 100 is capable of independent feeding of the optical fiber 10 into the bath with a speed less than, equal to or higher than the speed of the outer disposable guiding tube 40. Preferably, the metal coated optical fiber 10 is fed faster so that both the immersion end 50 of the outer disposable guiding tube 40 and leading section 10 of the metal coated optical fiber 10 arrive at the predetermined surface of the metal at approximately the same time. Once the bath level position is reached, the outer disposable guiding tube 40 is decelerated to a nearly stationary position in the molten metal 52. The leading section 10 of the metal coated optical fiber 10 continues to move slowly deeper in the steel at about 200 mm/s for approximately 0.7 seconds. Both the outer disposable guiding tube 40 and the metal coated optical fiber 10 are constantly moving at unequal speeds to avoid welding the two metal surfaces together, thereby solving a problem stated in the prior art.

The problem of the acceleration and deceleration of the metal coated optical fiber 10 is more complicated than moving the outer disposable guiding tube 40. The metal coated optical fiber 10 is constantly decoiled and recoiled from a coil or spool 20 with its coil weight that is constantly changing due to fiber consumption. The feeding machine, particularly the feeding device, is adapted with additional mechanics to avoid the elastic spring back effect from the coil or spool 20 itself as well as the weight of the pyrometer connected to the coil. For this reason, there are two servo motors or feeding motors 25, 45 to control the fiber movement. One feeding motor 25 takes care of the decoiling and recoiling of the metal coated optical fiber 10 and pre-feeds the metal coated optical fiber 10 in such a way that the feeding motor 25 can accelerate very fast.

The consumable metal coated optical fiber 10 receives the radiation light emitted from the molten metal, conveys such to a photo-electric conversion element mounted on the opposite end of the coiled consumable metal coated optical fiber 10 and, combined with associated instrumentation, measures the intensity of the radiation, using this to determine the temperature of the metal. The metal coated optical fiber coil or spool 20 and instrumentation are located at a distance away, and separated from the EAF, but are suitably robust to withstand the harsh conditions of the steel making environment. The location of the immersion end of the metal coated optical fiber 10 is constantly known and monitored by machine instrumentation throughout the immersion, measuring and removal portions of the immersion cycle. The machine is equipped with position encoders that determine the passage of metal coated optical fiber length and inductive switches that register the metal coated optical fiber end.

After the measurement is complete, both the consumable metal coated optical fiber 10 and the outer disposable guiding metal tube 40 are withdrawn from the steel with different speeds in such a way that the metal coated optical fiber 10 stays relatively deeper in the bath. During this movement, it is possible to determine the bath-level due to a change in the light intensity when correlated with the length of metal coated optical fiber 10 extracted between predetermined positions. The post measurement bath level determination is subsequently used for the next immersion. It is also contemplated that the bath level could be determined during immersion using various techniques well described in the literature without departing from the method of the present invention.

Once the metal coated optical fiber 10 is clear of the EAF interior, the direction of the outer disposable guiding tube 40 is reversed towards the furnace interior. The outer disposable guiding metal tube 40 is then ejected, disposed and consumed in the furnace interior. A new outer disposable guiding tube 40 and gas plug 30 are positioned to receive the metal coated optical fiber 10 for the next measurement. The remaining metal coated optical fiber 10 is recoiled during removal and returned to a starting position.

Some key abilities of the present invention are:
accurate payout and recoil of fiber;
detection of fiber end;
loading of outer disposable guiding tube;
guide fiber at starting position into gas plug;
fully reversible drives for both fiber and outer disposable guiding tube;
independent speed profits for fiber and outer disposable guiding tuber;
registration of fiber output for level detection; and
attachable to furnace shell for tilt compensation of bath level.

The method is described by way of example of a total cycle description. This concept should bring us to an operator free control of EAF's. It is envisioned that the best operation is to take multiple temperature immersions in quick succession (about five). Each immersion is approximately 2 second. The total cycle time should be less than 20 seconds during a single heat.

Figure 4:
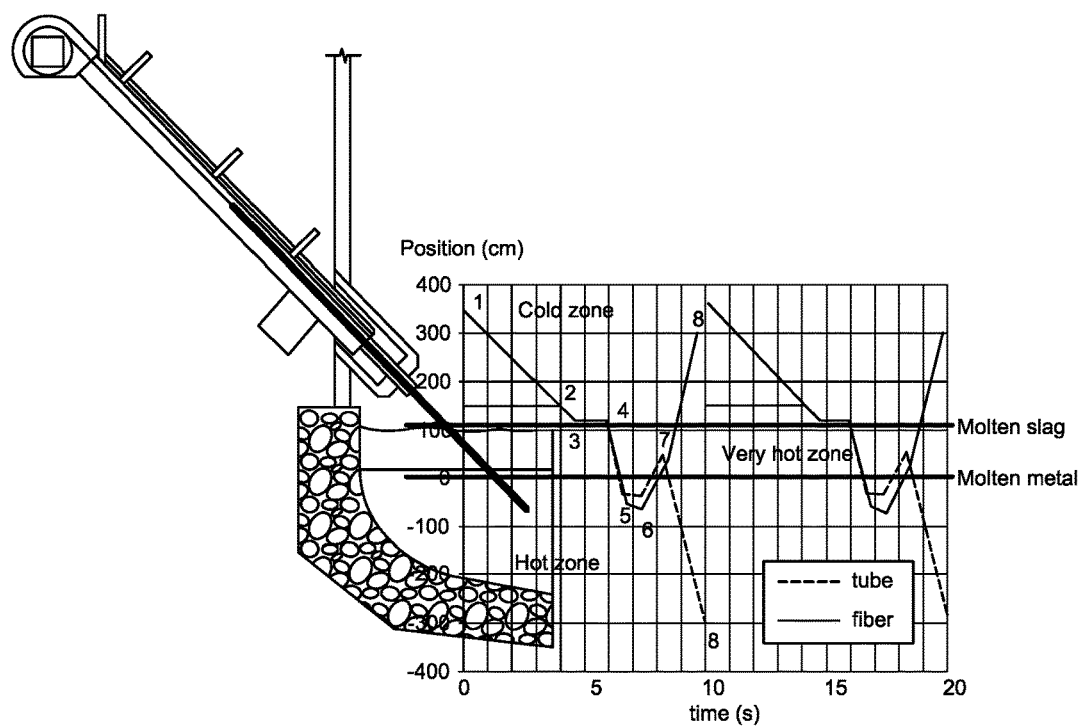
FIG. 4 shows a view of both the position of the immersion end of the outer tube and the immersion end of the optical fiber during immersion.

The schematic of FIG. 4 gives a view of both the position of the immersion end 50 of the outer disposable guiding tube 40 and the immersion end or leading section 10 of the metal coated optical fiber 10 during two immersions of a measurement cycle. For fiber movement, the end position of the fiber is tracked.

With tube movement, the position of the immersed end of the disposable guiding tube 40 is indicated. The opposite of the immersion end 50 of the outer disposable guiding tube 40 is the gas plug 30. For the purpose of this schematic, the outer disposable guiding tube 40 is already in ready to immerse position. Gas plug 30 is already attached to the back end and the metal coated optical fiber 10 is just inside the gas plug 30. The relative dimensions shown are for descriptive purposes, understanding that the absolute distances are predicated upon the actual furnace size which is a variable from steel shop to steel shop.

The starting position 1 at time 0 of the fiber within the outer metal tube is set at 350 cm above the molten metal/bath level. The starting position is outside of the furnace. The starting position 1 at time 0 of the immersion end of the outer metal tube is located at 150 cm above the bath level. The metal coated optical fiber 10 is fed from position 1 to position 2 while the outer disposable guiding tube 40 remains nearly stationary. Between time 0.8 seconds and 1.2 seconds covering positions 2 through 4, both the metal coated optical fiber 10 and the outer disposable guiding tube 40 advance to a location just above the molten slag 51. At 1.2 seconds and position 4, the fiber is advanced slightly faster than the outer disposable guiding metal tube 40 passing through the slag 51 and into the molten metal 52. The outer disposable guiding metal tube 40 slows while the metal coated optical fiber 10 advances at approximately 200 mm/s reaching the maximum immersion at position 6 and 1.5 seconds into the immersion. Both metal coated optical fiber 10 and outer disposable guiding tube 40 are extracted within 0.1 seconds. The metal coated optical fiber 10 continues to be withdrawn and recoiled returning to its load position 8 while the remains of the outer disposable guiding metal tube direction is reversed at position 7 and discarded. The metal coated optical fiber 10 is still protected by the remaining portion of the discarded outer disposable guiding tube 40.

Figure 5:
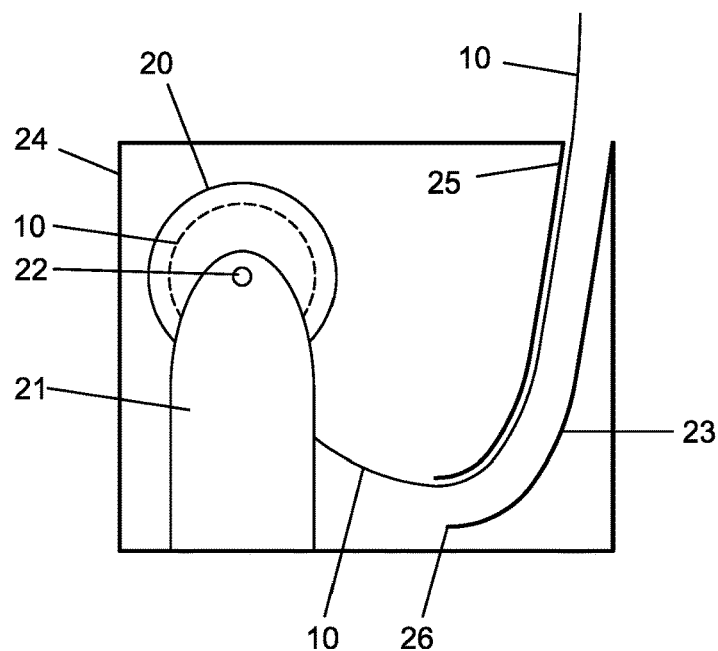
FIG. 5 shows a side view of the feeding device.

FIG. 5 is a side view of the feeding device for feeding the optical fiber 10 from the coil 20 and for recoiling unused fiber 10. The coil 20 is inserted into the support 21. The support 21 comprises an axis 22 for the coil so that the coil 20 can rotate around its axis 22. A flexible tube 23 acts as the load for avoiding a spring back effect of the optical fiber 10. The flexible tube 23 is a guide for the optical fiber as shown in FIG. 5. In other words, the fiber 10 is fed through the flexible tube 23.

The flexible tube 23 is formed from metal. The flexible tube may comprise a plurality of metal rings or metal sleeves which are connected to each other in a flexible manner. The upper end 25 of the flexible tube 23 is attached to the housing 24 of the feeding device. The opposite non-fixed end 26 is free to move and ends below the axis 22. As a result, at least a lower part flexible tube acts as load for the fiber 10 which avoids a spring back effect.

The inner diameter of the flexible tube 23 is at least five times larger than the outer diameter of the coated optical fiber 10. The housing 24 is a cabinet which covers and protects the support 21 for the coil 20 and the flexible tube 23.

The feeding device comprises an electrical motor drive (not shown) which can rotate the coil in a desired direction, especially for recoiling the fiber 10.

Figure 6:
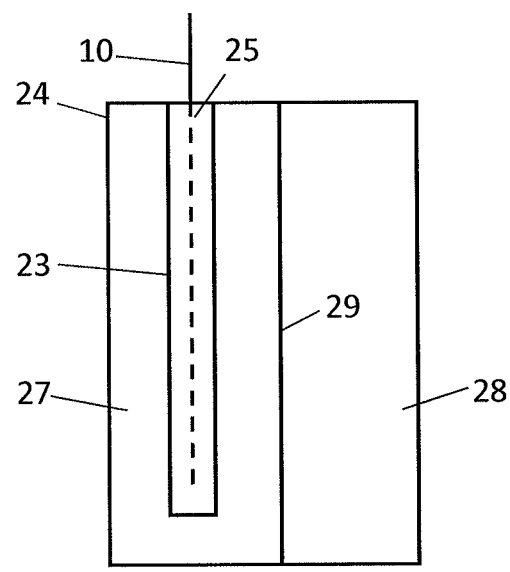
FIG. 6 shows a front view of the feeding device of FIG. 5.

FIG. 6 is front view of the feeding device. The cabinet 24 comprises a first accessible compartment 27 for the coil support and the flexible tube 23 and a second compartment 28 for an electrical equipment of the feeding device. The compartment 27 is separated from the compartment 28 by an inner wall 29. There is a door (not shown) for the compartment 27 which comprises the support and the flexible tube 23. The door is unlocked so that the compartment 27 is accessible for an end user. The compartment 28 for the electrical equipment of the feeding device comprises a door having a locking mechanism. Due to the locking mechanism, the compartment 28 for the electrical equipment is only accessible for authorized persons.

At least the first compartment for the support and the flexible tube 23 of the cabinet is air-conditioned. The feeding device comprises means for converting the light transmitted by the optical fiber into a temperature.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A feeding device for feeding an optical fiber (10) from a coil (20) and for recoiling unused fiber (10) for use in an apparatus (100) for measuring the temperature of a melt (52), the feeding device comprising:
a support for a coil;
a feeding mechanism for decoiling an optical fiber from the coil and for recoiling the optical fiber;
at least one motor for driving the feeding mechanism; and
a load for the optical fiber which is configured to avoid a spring back effect of the optical fiber from the coil,
wherein the load is a guide for the optical fiber (10) in the form of a flexible tube (23), and
wherein an upper end of the flexible tube is attached to a housing (24) of the feeding device, and the flexible tube comprises a non-fixed end (26) that ends below an axis (22) for the coil.

2. The feeding device according to claim 1, wherein the flexible tube (23) is formed from metal.

3. The feeding device according to claim 1, wherein an inner diameter of the flexible tube (23) is more than 10 mm.

4. The feeding device according to claim 3, wherein the inner diameter of the flexible tube (23) is at least five times larger than an outer diameter of the optical fiber (10).

5. The feeding device according to claim 1, wherein the housing (24) which covers the support (21) for the coil (20) and the load (23) for the optical fiber (10).

6. The feeding device according to claim 5, wherein the housing (24) is a cabinet comprising:
a first accessible compartment (27) for the support (21) for the coil and the load (23); and
a second compartment (28) for electrical equipment of the feeding device.

7. The feeding device according to claim 6, wherein the second compartment (28) comprising electrical equipment of the feeding device is configured to be closed by a lock of a door.

8. The feeding device according to claim 7, wherein the cabinet (24) is air-conditioned.

9. The feeding device according to claim 1, further comprising means for converting light transmitted by the optical fiber (10) into a temperature.

10. The feeding device according claim 1, further comprising a motor drive for the coil (20).

11. A robotic immersion device for measuring the temperature in a metallurgical vessel, the robotic immersion device comprising a feeding device according to claim 1.

12. A robotic immersion device according to claim 11, further comprising
a disposable guiding tube having an immersion end and a second end opposite to the immersion end,
wherein the optical fiber (10) can be partially arranged in the disposable guiding tube,
wherein an inner diameter of the disposable guiding tube is bigger than an outer diameter of the optical fiber (10),
wherein an elastic plug is arranged at the second end of or within the disposable guiding tube, and
wherein the optical fiber is fed through the elastic plug and the elastic plug reduces a gap between the optical fiber and the disposable guiding tube.

* * * * *